United States Patent [19]
Shih et al.

[11] Patent Number: 5,837,228
[45] Date of Patent: Nov. 17, 1998

[54] BIOERODIBLE IMPLANTS

[75] Inventors: Chung Shih; Gaylen M. Zentner; Randall V. Sparer, all of Lawrence, Kans.; R. Lee Seward, Watchung, N.J.

[73] Assignee: Merck & Co., Inc., Rahway, N.J.

[21] Appl. No.: 939,539

[22] Filed: Sep. 2, 1992

Related U.S. Application Data

[63] Continuation of Ser. No. 570,742, Aug. 22, 1990, abandoned.

[51] Int. Cl.$^6$ ................................. A61K 9/14; A61F 2/02
[52] U.S. Cl. ...................... 424/78.37; 424/422; 424/423; 424/426; 424/486; 514/953
[58] Field of Search ..................... 424/422, 423, 424/426, 486, 78.37; 514/953

[56] References Cited

U.S. PATENT DOCUMENTS

| | | | |
|---|---|---|---|
| 4,093,709 | 6/1978 | Choi et al. | 424/424 |
| 4,150,108 | 4/1979 | Graham | 424/22 |
| 4,221,779 | 9/1980 | Graham | 424/78 |
| 4,304,767 | 12/1981 | Heller et al. | 424/78 |
| 4,356,166 | 10/1982 | Peterson et al. | 424/19 |
| 4,636,387 | 1/1987 | Allcock et al. | 514/89 |
| 4,639,366 | 1/1987 | Heller | 424/78 |
| 4,745,161 | 5/1988 | Saudek et al. | 525/420 |
| 4,764,364 | 8/1988 | Heller et al. | 424/78 |
| 4,765,973 | 8/1988 | Heller et al. | 424/78 |

FOREIGN PATENT DOCUMENTS

WOA-89/05138  6/1989  WIPO .

OTHER PUBLICATIONS

Chemical Abstracts, *111, No. 16,* Abstract #140344a (1989).
Chow, A.W., Hamlin, R.D., Heller, J., "Cure Behavior of Neat and and Drug–Loaded Poly(ortho ester) Bioerodible Implants", Journal of Controlled Release, 9, 123–131 (1989).

*Primary Examiner*—Thurman K. Page
*Assistant Examiner*—C. Azpuru
*Attorney, Agent, or Firm*—Francis F. Bigley; Mark R. Daniel; Joseph F. DiPrima

[57] ABSTRACT

A bioerodible controlled release dosage form is disclosed comprising a polymer formed by condensing beneficial agents having a hydroxyl functionality of two or more with diketene acetals or divinyl ethers which delivers beneficial agents to a biological environment of use. A statistically significant portion of the beneficial agent is covalently bonded within the polymer matrix.

18 Claims, 3 Drawing Sheets

BIOERODIBLE IMPLANTS

This is a continuation of application Ser. No. 07/570,742 filed Aug. 22, 1990, now abandoned.

BACKGROUND OF THE INVENTION

Because of bioavailability, efficacy, or dosing convenience concerns, many beneficial agents are preferably administered parenterally. Since a recipient could receive several dosage forms over a lifetime, it is essential that the dosage form leave little or no undesirable residue. Bioerodible polymeric dosage forms are ideally suited for these applications, and provide the additional advantage that drug delivery from a single dosage form may effectively treat the disease state for a prolonged period.

Known bioerodible polymeric controlled release devices can be generally categorized as either encapsulated devices or matrix devices. In encapsulated devices, beneficial agent (e.g., drug) is surrounded by a polymer layer which controls release of the beneficial agent. The beneficial agent in a matrix device, however, is dissolved or suspended in the polymer matrix and diffuses through the matrix, or is released in conjunction with the dissolution, disintegration, decomposition, or erosion of the matrix.

With matrix devices, beneficial agents can be incorporated into the matrix by physical entrapment or are chemically bound to the matrix. When exposed to a biological environment of use, the polymer matrix dissolves, disintegrates, decomposes, or erodes (i.e., degrades) to release beneficial agent.

Known matrix devices in which the beneficial agent is chemically bound to the polymeric matrix are limited to compositions such as those of U.S. Pat. Nos. 4,356,166, 4,636,387, and 4,745,161, in which the beneficial agent is pendantly attached to the polymeric chains comprising the matrix rather than directly incorporated into the polymer chain backbone. Significantly, these known pendant polymer-beneficial agent schemes require a disadvantageous multi-step synthesis.

SUMMARY OF THE INVENTION

The instant invention provides bioerodible controlled release dosage forms which deliver beneficial agents to a biological environment of use for extended periods. The environment of use may be any anatomical site where the dosage form may be located to elicit the desired pharmacological response. Specifically, dosage forms of the present invention are formed by condensing beneficial agents such as drugs having a hydroxyl functionality of at least two and, if desired, other polyols, with diketene acetals or divinyl ethers (where the term polyol is employed throughout this specification, it implies a molecule with 2 or more hydroxyl groups). The resultant bioerodible polymeric dosage form comprises either a poly(ortho ester) or a polyacetal. An important feature of the polymeric dosage forms of the instant invention is that a statistically significant portion of the amount of monomeric beneficial agent is covalently incorporated into the resultant bioerodible polymer chain backbone, i.e., the beneficial agent is incorporated into the polymer backbone by means of hydrolytically labile ortho ester or acetal bonds.

U.S. Pat. No. 4,304,767 describes the synthesis of poly (ortho ester)s by condensation of diketene acetals and polyols. U.S. Pat. Nos. 4,150,108 and 4,221,779 describe condensation of divinyl ethers and polyols to form polyacetals. While none of these patents suggest the use of a beneficial agent (drug) as a polyol condensation monomer, their general disclosure of poly(ortho ester) and polyacetal synthesis, is incorporated herein by reference.

Representative examples of biologically active beneficial agents are drugs having two or more hydroxyl groups that can serve as condensation monomers in the synthesis of the bioerodible dosage form of the present invention and include anthelmintic agents from the general groups of compounds collectively known as the avermectins and milbemycins, including specific example compounds such as ivermectin, moxidectin, milbemycin-5-oxime and nemadectin. Representative of another type of anthelmintic is the compound bithional. Other beneficial agents possessing two or more hydroxy groups that may be covalently incorporated into the polymer matrix are: narcotics and narcotic antagonists such as morphine, nalorphine, naloxone, and naltrexone; antihistamines such as terfenadine; adrenergic agonists such as phenylephrine, terbutaline, albuterol, isoproterenol; adrenergic blockers such as nadolol, pindolol; sedative hypnotics such trichlofos, chlorhexadol; centrally acting agents such as mephenesin; analeptics such as picrotin; antiparkinson agents such as L-dopa/carbidopa; steroids such as digoxin, prednisone, triamcinolone, dexamethasone, beclomethasone, estradiol, ethinyl estradiol, fluoxymesterone; coronary vasodilators such as dipyridamole; anticoagulants such as dicumarol and heparin; antihypertensives such as α-methyldopa and labetalol; antiinflammatory/antirheumatic agents such as osalazine and aurothioglucose; cholesterol reducing agents such as probucol and HMG-COA reductase inhibitors such as pravastatin, or lovastatin and simvastatin in the open hydroxy acid form; antibiotics such as doxycycline, minocycline, erythromycin, clindamycin, gentamicin, tobramycin, spectinomycin, mithramycin, rifampin; antifungal agents such as amphotericin B, nystatin; antiviral agents such as vidarabine, idoxuridine; bone growth promotants such as prostaglandin $E_2$; anticancer agents such as streptozocin, doxorubicin, vinca alkaloids; and, vitamins such as pyridoxamine and riboflavin. The above list is not meant to be exhaustive. Any beneficial agent with two or more hydroxyl groups is within the scope of the invention. It is known to the art that beneficial agents can be synthesized as various forms of prodrugs which may contain two or more hydroxyl groups and, therefore, are included. Depending on its specific therapeutic role the beneficial agent may provide prophylactic therapy and/or treatment of an existing condition.

The following schemes illustrate the condensation reaction of beneficial agent and other monomeric polyols with diketene acetals and divinyl ethers to form bioerodible poly(ortho ester)s and polyacetals, respectively:

Scheme 1

Poly(ortho ester)s

-continued
Scheme 1

| | |
|---|---|
| R is | H, alkyl, aryl (R groups may be the same or different); |
| R" is | quadrivalent carbon or grouping; |
| D(OH)$_a$ is | beneficial agent or drug; |
| R'(OH)$_b$ is | polyol; |
| a is | 2 or greater; |
| b is | 2 or greater; |
| A is | |

| | |
|---|---|
| x is | mer units with (a = 2) |
| y is | mer units with (b = 2) |
| z is | mer units with (b = 3) (R' in z-type mer units may be substituted in part by D in cases where D possesses 3 or more hydroxyls). |

Scheme 2

Polyacetals $D(OH)_a + R'(OH)_b \longrightarrow$ $(A-D)_x(A-R')_y(A-R')_z$
                              |
                              A—

| | |
|---|---|
| R is | covalent linkages or alkylene which may optionally contain heteroatoms (see U.S. Pat. Nos. 4,150,108 and 4,221,779); |
| D(OH)$_a$ is | beneficial agent or drug; |
| R'(OH)$_b$ is | polyol; |
| a is | 2 or greater; |
| b is | 2 or greater; |
| A is | |

| | |
|---|---|
| x is | mer units with (a = 2); |
| y is | mer units with (b = 2); |
| z is | mer units with (b = 3) (R' in z-type mer units may be substituted in part by D in cases where D possesses 3 or more hydroxyls.) |

DETAILED DESCRIPTION OF A PREFERRED EMBODIMENT

Figure 1:
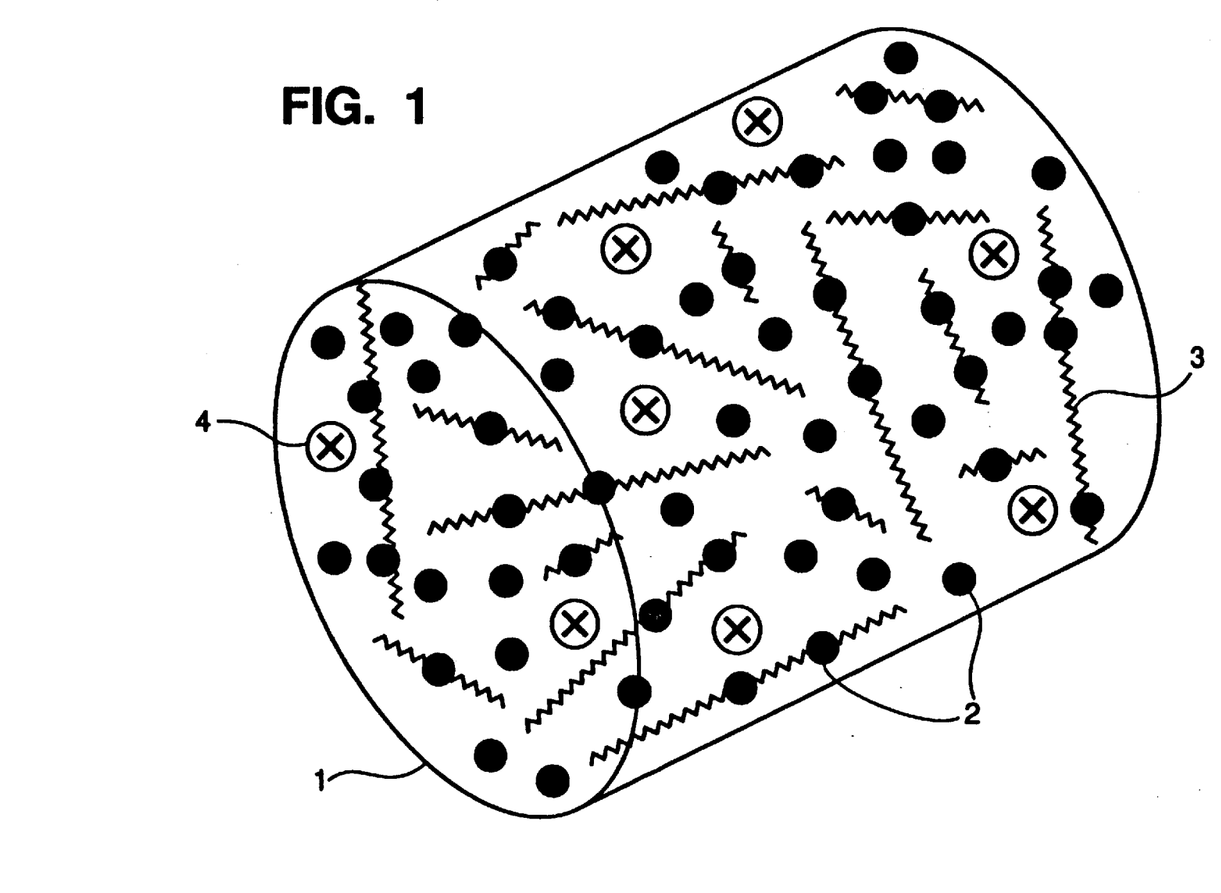
FIG. 1 depicts a rod-shaped implant manufactured in accordance with the present invention.
Figure 2:
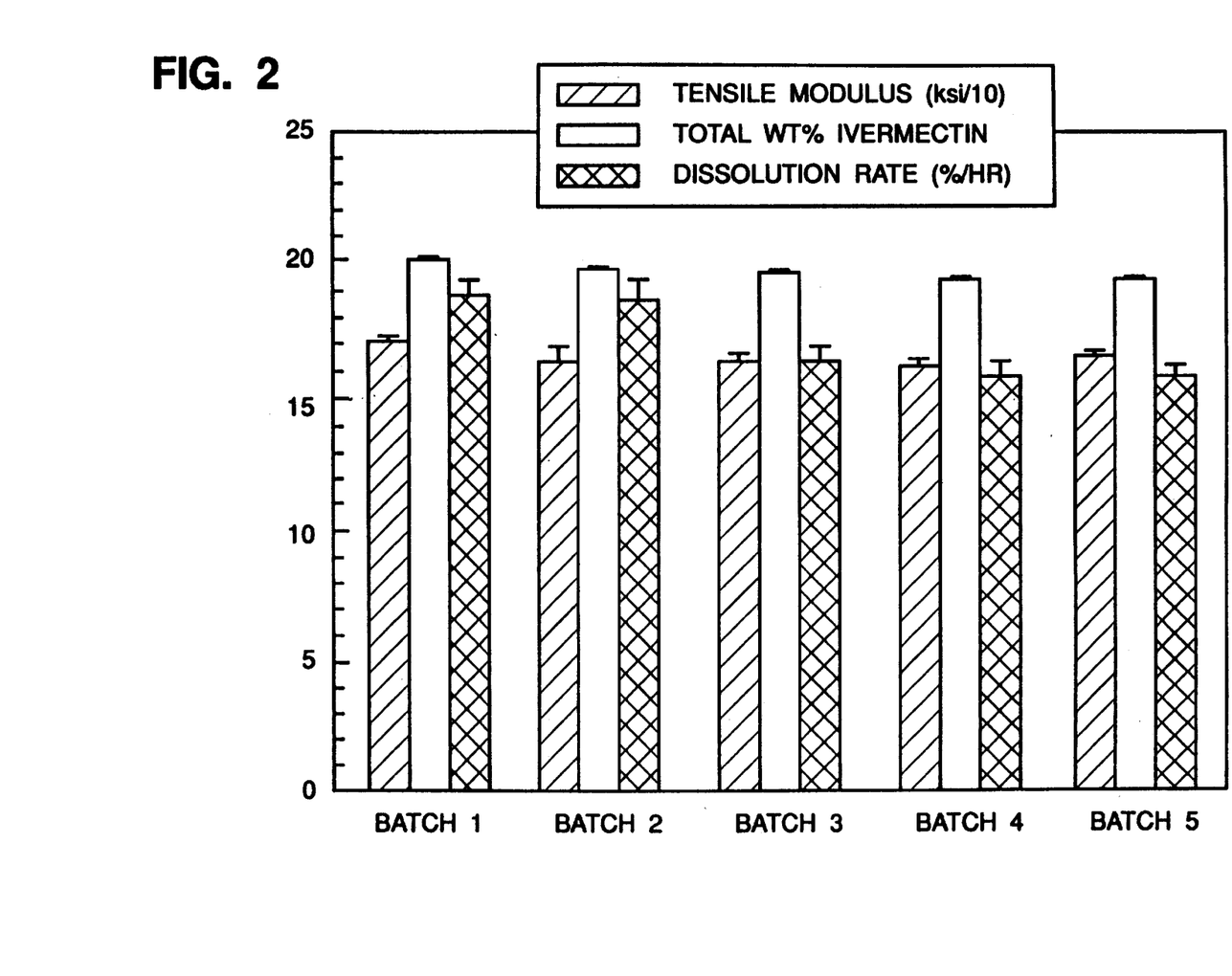
FIG. 2 plots tensile modulus, weight percentage of beneficial agent and dissolution rate for implants made in accordance with the present invention.

The instant invention may be shaped in numerous geometric configurations. A rod-shaped device, 1, is illustrated in FIG. 1. When sized at 0.5 mm to 5 mm diameter and 0.5 to 10 cm in length this shape is readily suited for implantation, although larger and smaller dimensions are within the scope of the invention. The beneficial agent (frequently a drug), 2, is to a substantial degree covalently incorporated into the backbone of the polymer chains comprising the bioerodible matrix, 3, with a portion of the total drug also dispersed throughout the matrix. Other additives, 4, such as stabilizers, antioxidants and catalysts may be optionally included. The bioerodible controlled release dosage form is implanted intramuscularly, subcutaneously or intraperitoneally. If desired, more than one implant may be inserted.

In a preferred embodiment, a poly(ortho ester) implant is synthesized by a condensation reaction of polyol monomers, including the polyol anthelmintic drug ivermectin, with a diketene acetal to form a potent implantable dosage form useful against various developmental stages of *Dirofilaria immitis,* a filarial parasite and causative organism of canine heartworm disease. Specifically, ivermectin and various combinations of other polyols such as 1,6-hexanediol, 1,7-heptanediol, tetraethylene glycol, triethylene glycol, and 1,2,6-hexanetriol were covalently reacted with the diketene acetal 3,9-bis-(ethylidene)-2,4,8,10-tetraoxaspiro[5,5] undecane (viz., DETOSU) to form a poly(ortho ester) matrix. Ivermectin is a polyol with three hydroxyl groups, and therefore reacts with the DETOSU. A significant portion (20 to 60%) of the ivermectin was covalently incorporated into the poly(ortho ester) chains. This dosage form provides prophylactic levels of ivermectin for periods ranging from three to fifteen months with a single dose. This dosage form can be administered to a recipient by simple subcutaneous injection. This implant is biodegradable and completely erodes within the animal while releasing drug, thus ensuring that accumulation of implants is minimized with repeat dosings.

Anthelmintic beneficial agents other than ivermectin, such as C-076 avermectin derivatives, milbemycins and closely related compounds such as nemadectin and moxidectin, which contain two or more hydroxyl groups can be utilized in the instant preferred embodiment of the invention. These agents are disclosed in the following U.S. Patents: U.S. Pat. No. 4,199,569, Chabala et al, Selective Hydrogenation Products (Ivermectin); U.S. Pat. No. 4,200,581, Fisher et al, Alkyl Derivatives; U.S. Pat. No. 4,201,861, Mrozik et al, Acyl Derivatives; U.S. Pat. No. 4,203,976, Fisher et al, Carbohydrate Derivatives; U.S. Pat. No. 4,206,205, Mrozik et al, Monosaccharide and Aglycone Derivatives; U.S. Pat. No. 4,289,760, Mrozik et al, 23-keto Derivatives; U.S. Pat. No. 4,427,663, Mrozik et al, 4"-keto and 4"-Amino Derivatives; U.S. Pat. No. 4,469,682, Mrozik, Phosphate Esters; U.S. Pat. No. 4,530,921, Mrozik, Epoxide Derivatives; Re 32006, Chabala et al, 13-Halo and 13-Deoxy Derivatives; U.S. Pat. No. 4,547,491, Mrozik et al, C8a Oxo Derivatives; Re 32034, Chabala et al, 13-Halo and 13-Deoxy Derivatives; U.S. Pat. No. 4,579,864, Linn et al, 13-Keto, 13-Imino and 13-Amino Derivatives; U.S. Pat. No. 4,581,345, Wyvratt, 8,9-Cyclopropyl Derivatives; U.S. Pat. No. 4,587,247, Linn et al, 13-Poly alkoxy Derivatives; U.S. Pat. No. 4,622,313, Wyvratt, O-Sulfate Derivatives; U.S. Pat. No. 4,806,527, Christensen et al, Δ26,27-Alkyl Derivatives; U.S. Pat. No. 4,831,016, Mrozik et al, Reduced Derivatives; U.S. Pat. No. 4,833,168, Wyvratt, Reformatsky Adducts; U.S. Pat. No. 4,873,224, Linn et al, 4',4"-Semicarbazone, hydrazone etc. Derivatives; U.S. Pat. No. 4,874,749, Mrozik, 4"-M-methyl Amino Derivatives; U.S. Pat. No. 4,895,837, and Mrozik et al, Δ23,24 Derivatives; U.S. Pat. No. 4,897,383, Sinclair, 3',3" Des methoxy Derivatives; and U.S. Pat. No. 3,950,360, Aoki et al, Milbemycin natural products. The following European patents also apply: EP 110,667, Ide et al, Milbemycin-5-oxime derivatives; EP 214,731, Gibson et al, 25-substituted milbemycin compounds; and EP 170006, Wood et al, 25-substituted milbemycin compounds.

It will also be appreciated that the present invention will be useful in the treatment of parasitic diseases in humans and a variety of animals such as swine, sheep, horses, cattle, goats, dogs, cats and poultry.

The avermectin and milbemycin compounds described in the above references, and which may be incorporated as a beneficial agent in the implant of the present invention, are particularly effective against endo or ecto parasites, of animals and man, that feed on or are associated with blood, body secretions or tissues, such as developing larvae of *Dirofilaria immitis* in dogs and cats. Other endoparasites of dogs and cats particularly hookworms, *Ancylostoma caninum, Ancyclostoma tubaeforma, Ancylostoma braziliense,* and *Uncinaria stenocephala,* and whipworms *Trichuris vulpis* are likely targets. Ascarids, such as *Toxocara canis, Toxocara cati,* and *Toxascaris leonina,* are also potential targets, as are the threadworms *Strongyloides stercoralis* and lungworms *Capillaria sp.* and *Aelurostrongylus sp.* Ecto parasites particularly ear mites otodectes cynotis, other mites, fleas and ticks may also be affected.

The implant can be synthesized and fabricated as either a linear polymer or crosslinked polymer erodible matrix. The techniques used in fabricating the implant will vary. Linear (thermoplastic) polymers can be synthesized and then reheated at a later time for compounding with additives (e.g., stabilizers and antioxidants). This mixture can then be reheated at a later time for molding into the final shape. When processing a crosslinked polymer implant, all monomers (including the beneficial agent) and additives are added to the polymerization reaction prior to complete polymerization. Since crosslinking agent(s) is/are present, the mixture cannot be easily molded once the polymerization reaction is completed. It is preferred that the implant be shaped and molded prior to complete cure. Both continuous and batch processing procedures are applicable.

Ivermectin/Poly(Ortho Ester) Implants

Ivermectin has been incorporated into a crosslinked poly(ortho ester) erodible polymer and utilized as an implant for the control of parasites. The implant is manufactured in three stages: 1) Synthesis of a partially polymerized poly(ortho ester) paste containing the homogeneously mixed additives; 2) Dispensing of the paste into rod-shaped molds; and, 3) Curing and removal of the completely polymerized rods from the molds. The poly(ortho ester) was a condensation polymer comprised of two fundamental types of monomers: polyols (e.g., 1,6-hexanediol, tetraethylene glycol, 1,2,6-hexanetriol, ivermectin) and a diketene acetal (e.g., DETOSU). It is known that ortho ester bonds are substantially more stable to hydrolysis under basic pH conditions. The addition of an ortho ester bond stabilizer such as MgO or Mg(OH)$_2$ which results in an alkaline pH, substantially modified (slowed) the erosion process. In this invention, the beneficial agent (ivermectin) of a preferred embodiment was also a polyol and reacted as a monomer with the DETOSU to become covalently bonded within the poly(ortho ester) backbone. A statistically significant portion (1 to 100%) of the total drug covalently bonded within the polymer backbone is within the scope of the invention, with typical values of 20 to 60% bonded. This provides the advantage that the bonded ivermectin cannot diffuse out of the dosage form until it is hydrolytically cleaved from the crosslinked poly(ortho ester).

The thermal, mechanical and drug release performance of the poly(ortho ester)/ivermectin implant was controlled by the amounts of DETOSU, stabilizer, and ivermectin, and the amounts and types of polyols (diols and crosslinkers) in the formulation. Suitable polyols, stabilizers, and polymerization stoichiometries are as follows:

I. Polyols
  1. Diols with a structure of HO—R—OH, where R is:
     a. a linear hydrocarbon chain with a total carbon number of 2 to 20; specifically exemplifying such diols are 1,4-butanediol, 1,5-pentanediol, 1,6-hexanediol, 1,7-heptanediol, 1,8-octanediol, 1,9-nonanediol, 1,10-decanediol, and the like.
     b. a branched hydrocarbon chain with a total carbon number between 4 and 20; specifically exemplifying such diols is 3,3-dimethylpentanediol.
     c. a cyclic hydrocarbon with a total carbon number between 3 and 20; specifically exemplifying such diols is cyclohexane dimethanol.
     d. a hydrocarbon residue containing heteroatoms such as oxygen, nitrogen, and/or sulfur in the main chain or oxygen, nitrogen, halide, and/or sulfur in a side group. Specifically exemplifying such diols are triethylene glycol, tetraethylene glycol, n-butyldiethanolamine, polyethylene glycols, and the like.
     e. structures 1a. through 1d. wherein one or more of the carbons in R are replaced by silicon.
  Combinations of diols with structures as described in 1a. through 1e. are within the scope of the invention.
  2. Crosslinkers with a structure R'(OH)$_m$, where m≧3 and R' is:
     a. a linear hydrocarbon chain with a total carbon number of 3 to 20.
     b. a branched hydrocarbon chain with a total carbon number between 4 and 20.
     c. a cyclic hydrocarbon with a total carbon number between 3 and 20.
     d. a hydrocarbon residue containing heteroatoms such as oxygen, nitrogen, and/or sulfur in the main chain or oxygen, nitrogen, halide and/or sulfur in a side group.
     e. structures 2a. through 2d. wherein one or more of the carbons are replaced by silicon.
  Combinations of crosslinkers with structures as described in 2a. through 2e. are within the scope of the invention. Specific examples of crosslinking agents include 1,2,6-hexanetriol, tromethamine, glycerol, pentaerythritol, 2-ethyl-2-hydroxymethyl-1,3-propanediol, glucose, and 1,3,5-cyclohexanetriol. Halide is F, Cl, Br, or I.

II. Stabilizers
  Oxides and hydroxides such as MgO, Mg(OH)$_2$, CaO, and Ca(OH)$_2$, carbonates and bicarbonates such as CaCO$_3$, MgCO$_3$, Na$_2$CO$_3$, and NaHCO$_3$, and organic amines such as tromethamine and triethylamine act to stabilize the polymer bonds and slow the hydrolytic breakdown.

III. Stoichiometry and Loading Specifications
  The stoichiometry is defined as the ratio of equivalents of ketene acetal or vinyl ether to equivalents of hydroxyl. Stoichiometries of 0.1 to 1.5 are applicable with preferred stoichiometries of 0.7 to 1.2. Hydroxyls are contributed by diols, crosslinkers, and beneficial agents. The diols and crosslinkers may be blended in any ratio as needed to give the final desired polymer properties. Crosslinker loadings are 0.1 to 100 mole percent of the total hydroxyl equivalents contributed by reagents other than the beneficial agent with a preferred crosslinker loading of 15 to 50 mole percent. Stabilizer(s) are loaded at 0.01 to 20 percent of the total dosage form weight with preferred loadings of 1 to 10%. Beneficial agent (drug) loadings between 0.1 to 50 percent of the total dosage form weight are typical with higher and lower loads within the scope of the invention. Of the total beneficial agent load, 1 to 100% is covalently incorporated into the polymer backbone.

IV. Antioxidants

Antioxidants, for example butylated hydroxytoluene (BET), may also be utilized in the present invention in small (usually <1% of total device weight) quantities.

V. Manufacture

Water can compete with the polyols and drug for reaction with DETOSU and skew the stoichiometry of the polymerization. Therefore, it is preferable to polymerize in a dry atmosphere using reagents with low residual water contents. All weighing, transferring, polymerizing, mixing, device curing and handling should be undertaken in a controlled low humidity environment ($\leq$30% relative humidity is preferred).

Condensation polymerizations require pure monomers to maximize polymer molecular weights. The monomers used to fabricate the implant are polyfunctional. If there are monofunctional impurities in the reagents, the polymerization will be prematurely terminated and the erosion rate of the poly(ortho ester) may be altered. Monomers with purities $\geq$90% are desired and monomers of purity $\geq$98% are generally preferred.

It is preferred that the ivermectin/poly (ortho ester) crosslinked implant be synthesized by a batch fabrication process where the ivermectin is present during the bulk polymerization reaction. This will allow the ivermectin to be covalently incorporated into the poly(ortho ester) backbone. Example 1 describes the synthesis of such an implant. The stoichiometry of the reaction was within the preferred range of 0.7 to 1.2. The polyols (tetraethylene glycol, 1,6-hexanediol, and 1,2,6-hexanetriol), ivermectin, stabilizer (MgO) and antioxidant (BHT, if present) were pre-mixed. The DETOSU (diketene acetal) was then added to begin the polymerization reaction. The MgO is not soluble in this mixture. During this reaction/mixing step, the polymer simultaneously increased in molecular weight and degree of crosslinking. The resulting paste must not be completely polymerized or it will be too viscous (>2,000,000 cp) to extrude into the preferred molds. However, if the mixture is <2,000 cp the insoluble MgO stabilizer may settle out during cure. This could produce implants with irreproducible erosion. Typically, a viscosity of 5,000 to 50,000 cp (20° C.; 10 sec$^{-1}$) resulted in good suspension and uniformity of the MgO and permitted room temperature molding. This viscous reaction mixture was dispensed into molds to form the implant rods. A preferred mold is fluorinated hydrocarbon polymeric tubing (FEP tubing 1.6 mm o.d., 0.7 to 0.9 mm i.d.). The dispenser was a stainless steel piston and cylinder which, when loaded with the paste was hydraulically pressurized to force the paste into the mold tubes attached to the bottom of the cylinder. The filled tubes were cured in a low humidity environment at a controlled elevated temperature to complete the polymerization. The cured rods were removed from the tubes and cut to the proper length prior to packaging.

The invention is further illustrated by the following Examples.

EXAMPLE 1

An Atlantic Research 2CV Helicone Mixer was heated to 60° C. in a low humidity room (approximately 70° F. and 5% RH). Tetraethylene glycol (5.5702 gm), 1,6-hexanediol (3.3899 gm), 1,2,6-hexanetriol (2.0437 gm), magnesium oxide (0.8957 gm), and ivermectin (7.1997 gm, pre-dried under vacuum to reduce residual solvents) were added to the mixer and stirred for 1 minute. DETOSU (16.9229 gm) was added as a liquid to the mixture and was stirred at a moderate speed (setting "6") for 60 minutes at which time the mixture had a viscosity of 16,600 cp (20° C.; 10 sec$^{-1}$). It was dispensed into FEP teflon tubing and cured for 22.5 hours at 60° C. The poly(ortho ester) implants were removed from the tubing after cooling to room temperature. The implants contained 19.5±0.09 wt % total ivermectin by content, and 46.8%±0.84 of that was bound to the polymer matrix.

EXAMPLE 2

An Atlantic Research 2CV Helicone Mixer was heated to 60° C. in a low humidity room (approximately 70° F. and 5% RH). Tetraethylene glycol (3.7141 gm), 1,6-hexanediol (2.2603 gm), 1,2,6-hexanetriol (1.3696 gm) and magnesium oxide (0.6049 gm) were added to the mixer and stirred for 1 minute. DETOSU (11.3344 gm) was added as a liquid to the mixture and was stirred at a moderate speed (setting "6") for 45 minutes. Ivermectin (4.7963 gm, pre-dried under vacuum to reduce residual solvents) was then added and mixed for 45 minutes at 40° C. at which time the mixture had a viscosity of 16,900 cp (20° C.; 10 sec$^{-1}$), It was dispensed into PEP teflon tubing and cured for 18.5 hours at 60° C. The poly(ortho ester) implants were removed from the tubing after cooling to room temperature. The implants contained 18.8±0.07 wt % total ivermectin by content, and 38.4%±3.16 of that was bound to the polymer matrix.

EXAMPLE 3

An Atlantic Research 2CV Helicone Mixer was heated to 50° C. in a low humidity room (approximately 70° C. and 5% RH). Tetraethylene glycol (5.5637 gm), 1,6-hexanediol (3.3848 gm) and DETOSU (5.0397 gm) were reacted to form a prepolymer predominantly containing hydroxyl end groups. Mixing proceeded for 60 minutes at a moderate speed (setting "4"). Ivermectin (7.1877 gm, pre-dried under vacuum to reduce residual solvents), 1,2,6-hexanetriol (2.0356 gm) and magnesium oxide (0.8986 gm) were added to the mixer and stirred at a fast speed (setting "9") at 35° C. for 15 minutes. The balance of the DETOSU (11.8118 gm) was added as a liquid to the mixture and stirred at a moderate speed (setting "4") for 15 minutes at 35° C. at which time the mixture had a viscosity of 20,100 cp (20° C.; 10 sec$^{-1}$). It was dispensed into FEP teflon tubing and cured for 22 hours at 60° C. The poly(ortho ester) implants were removed from the tubing after cooling to room temperature. The implants contained 18.0±0.11 wt % total ivermectin by content, and 60.5%±4.29 of that was bound to the polymer matrix.

EXAMPLE 4

An Atlantic Research 2CV Helicone Mixer was heated to 35° C. in a low humidity room (approximately 70° F. and 5% RH). Tetraethylene glycol (3.9264 gm), 1,6-hexanediol (2.3887 gm) and DETOSU (11.9329 gm) were reacted to form a prepolymer predominantly containing ketene acetal end groups. Mixing proceeded for 1 minute at a moderate speed (setting "4"), and then magnesium oxide (0.6343 gm) was added and mixed for 9 minutes more. Ivermectin (5.0630 gm, pre-dried under vacuum to reduce residual solvents) was added to the mixer and stirred at a fast speed (setting "9") at 35° C. for 10 minutes. The 1,2,6-hexanetriol crosslinker (1.4634 gm) was added and mixing at the fast speed continued for 10 minutes at which time the mixture had a viscosity of 13,900 cp (20° C.; 10 sec$^{-1}$). It was dispensed into FEP teflon tubing and cured for 22 hours at 60° C. The poly(ortho ester) implants were removed from the tubing after cooling to room temperature. The implants contained 17.5±0.14 wt % total ivermectin by content, and 35.3%±1.62 of that was bound to the polymer matrix.

EXAMPLE 5

This example describes the manufacture and in vitro/in vivo testing of an ivermectin/poly(ortho ester) implant formulated to protect dogs from *D. immitis* heartworm infestation for up to 6 months.

An Atlantic Research 2CV Helicone Mixer was heated to 50° C. in an enclosed working area (approximately 70° F./30% RH). Tetraethylene glycol (15.5944 gm), 1,6-hexanediol (9.4881 gm), BHT (0.0203 gm), 1,2,6-hexanetriol (5.7562 gm), magnesium oxide (2.5025 gm), and ivermectin (20.0176 gm, pre-dried under vacuum to reduce residual solvents) were added to the mixer and stirred for 1 minute. DETOSU (46.7429 gm) was added as a liquid to the mixture and was stirred at a moderate speed for 60 minutes. The mixture was dispensed into FEP teflon tubing (0.73 mm I.D.) and cured for 19.5 hours at 60° C. The poly(ortho ester) implants were removed from the tubing after cooling to room temperature. The implants contained 21.4 wt %±0.21 total ivermectin by content, and 26.4%±4.71 of that total was bound to the polymer matrix. Tensile testing with an Instron 1130 Tensile Tester at 5 cm/minute gave a Young's modulus of 155.6±3.1 ksi and a tensile strength of 6.5±0.3 ksi. The glass transition temperature was 43.1±0.46° C. as measured by thermomechanical analysis (Perkin Elmer TMA-7) at 100 mN, 10° C./minute. A quality control in vitro dissolution test was performed at 37° C. using the rotating bottle method (NE XIV) and a dissolution medium of 0.5M sodium chloride and 0.5M sodium acetate (adjusted to pH 5.0 with HCl) in 30% aqueous isopropanol. The in vitro ivermectin release rate was 22.1±1.05%/hour and the lag time was 0.4±0.13 hours. This batch was implanted subcutaneously in beagle dogs at a dose of 1 cm of implant for each 5 kg of dog weight and demonstrated efficacy against challenges of infective *D. immitis* heartworm larvae at the time of implantation and at 3 months, 6 months or 9 months post-implantation of a single implanted dosage form.

EXAMPLE 6

Figure 3:
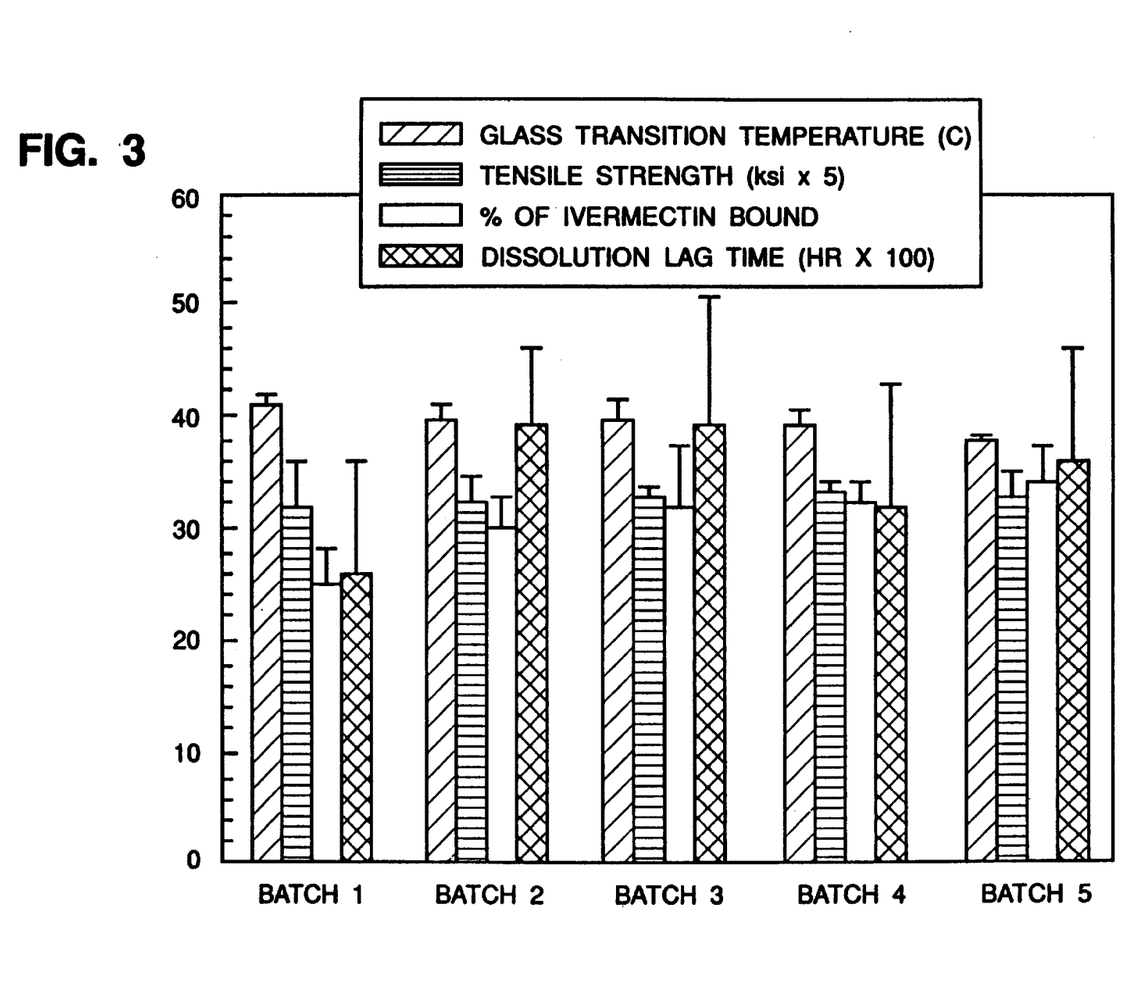
FIG. 3 plots glass transition temperature, tensile strength, weight percent of beneficial agent, and dissolution lag-time for implants made in accordance with the present invention.

Reproducible manufacture was demonstrated based on the physical properties and in vitro drug release performance of five batches of ivermectin/poly(ortho ester) implants fabricated according to the method in Example 5. Each batch was fabricated in a room at 70° F. at relative humidities between 15% and 25%. FIGS. 3 and 4 show the similarities among the five batches in the tensile modulus, tensile strength, dissolution rate, dissolution lag-time, glass transition temperature, ivermectin loading, and % of ivermectin bound to the polymer.

EXAMPLE 7

An ivermectin/poly(ortho ester) implant is prepared according to procedures outlined in Example 5 with the following reagents:

| | |
|---|---|
| 11.16 g | tetraethylene glycol |
| 12.61 g | 1,6-hexanediol |
| 0.02 g | BHT |
| 5.88 g | 1,2,6-hexanetriol |
| 2.50 g | magnesium oxide |
| 20.00 g | ivermectin |
| 47.83 g | DETOSU |

EXAMPLE 8

An ivermectin/poly(ortho ester) implant is prepared according to procedures outlined in Example 5 with the following reagents:

| | |
|---|---|
| 6.54 g | tetraethylene glycol |
| 15.90 g | 1,6-hexanediol |
| 0.02 g | BHT |
| 6.03 g | 1,2,6-hexanetriol |
| 2.50 g | magnesium oxide |
| 20.00 g | ivermectin |
| 49.01 g | DETOSU |

EXAMPLE 9

An ivermectin/poly(ortho ester) implant is prepared according to procedures outlined in Example 5 with the following reagents:

| | |
|---|---|
| 20.57 g | 1,6-hexanediol |
| 0.02 g | BHT |
| 6.22 g | 1,2,6-hexanetriol |
| 2.50 g | magnesium oxide |
| 20.00 g | ivermectin |
| 50.69 g | DETOSU |

EXAMPLE 10

An ivermectin/poly(ortho ester) implant is prepared according to procedures outlined in Example 5 with the following reagents:

| | |
|---|---|
| 22.31 g | 1,7-heptanediol |
| 0.02 g | BHT |
| 6.03 g | 1,2,6-hexanetriol |
| 2.50 g | magnesium oxide |
| 20.00 g | ivermectin |
| 49.14 g | DETOSU |

EXAMPLE 11

An ivermectin/poly(ortho ester) implant is prepared according to procedures outlined in Example 5 with the following reagents:

| | |
|---|---|
| 19.91 g | 1,6-hexanediol |
| 0.02 g | BHT |
| 6.02 g | 1,2,6-hexanetriol |
| 2.50 g | magnesium oxide |

-continued

| | |
|---|---|
| 20.00 g | ivermectin |
| 51.55 g | DETOSU |

EXAMPLE 12

An ivermectin/poly(ortho ester) implant is prepared according to procedures outlined in Example 5 with the following reagents:

| | |
|---|---|
| 14.68 g | 1,6-hexanediol |
| 0.02 g | BHT |
| 11.11 g | 1,2,6-hexanetriol |
| 2.50 g | magnesium oxide |
| 20.00 g | ivermectin |
| 51.69 g | DETOSU |

EXAMPLE 13

A polyacetal/ivermectin biodegradable polymer is produced by the procedures outlined in Example 5 by substituting 3,4-dihydro-2H-pyran-2-methyl-3,4-dihydro-2H-pyran-2-yl carboxylate for DETOSU (vinyl ether/hydroxyl stoichiometry=0.1 to 1.5).

EXAMPLE 14

A poly(ortho ester)/ivermectin biodegradable polymer is produced by the procedures of Example 5 by substituting HO—Si(CH$_3$)$_2$—(CH$_2$)$_4$—Si(CH$_3$)$_2$—OH for 1,6-hexanediol.

What is claimed is:

1. A bioerodible controlled release dosage form comprising:
   (a) a bioerodible polymer selected from a poly(ortho ester) or polyacetal in which from 1% to 100% of a biologically active ingredient, containing at least 2 hydroxyl groups, is covalently incorporated into a chain backbone of the polymer, wherein
      (i) during a condensation reaction, the viscosity of the mixture is maintained between 2,000 cp and 2,000,000 cp at 20° C. and 10 sec$^{-1}$ prior to extrusion into a mold; and wherein
      (ii) the total equivalents of hydroxyl are present in stoichiometric ratios of 1 equivalent of hydroxyl to 0.1 to 1.5 equivalents of ketene acetal or vinyl ether, and
   (b) wherein the biologically active ingredient is
      (i) present at a level between 0.1 to 50% of the total dosage form weight; and
      (ii) capable of being released from the polymer into the environment of use.

2. The dosage form of claim 1 wherein the biologically active ingredient, containing a hydroxyl functionality of at least two, is selected from the group consisting of:
   (a) anthelmintic agents;
   (b) narcotics and narcotic antagonists;
   (c) antihistamines;
   (d) adrenergic agents;
   (e) adrenergic blockers;
   (f) sedative hypnotics;
   (g) CNS agents;
   (h) analeptics;
   (i) antiparkinson agents;
   (j) steroids;
   (k) coronary vasodilators;
   (l) anticoagulants;
   (m) antihypercholesterolemics;
   (n) antibiotics;
   (o) antifungal agents;
   (p) antiviral agents;
   (q) bone growth promotants;
   (r) anticancer agents;
   (s) vitamins;
   (t) antiinflammatory agents;
   (u) antihypertensive agents.

3. The dosage form of claim 2 wherein the beneficial agent is an anthelmintic selected from the group consisting of:
   a) avermectins;
   b) milbemycins.

4. The dosage form of claim 3 wherein the polymer further comprises in addition to the beneficial agent one or more other polyol monomer residues covalently incorporated into the polymer.

5. The dosage form of claim 4 wherein the beneficial agent is selected from:
   a) ivermectin;
   b) moxidectin;
   c) nemadectin;
   d) milbemycin-5-oxime.

6. The dosage form of claim 5 wherein each polyol monomer is independently selected from the group consisting of:
   (a) a linear hydrocarbon with 2 to 20 carbons and 2 hydroxyls;
   (b) a cyclic hydrocarbon with 3 to 20 carbons and 2 hydroxyls;
   (c) a linear or cyclic hydrocarbon with 3 to 20 carbons and 3 or more hydroxyls;
   (d) a branched hydrocarbon with 4 to 20 carbons and 2 or more hydroxyls;
   (e) acyclic or cyclic compounds of groups (a), (b), (c) and (d) containing one or more heteroatoms selected from the group consisting of:
      (i) oxygen, other than as hydroxyl;
      (ii) nitrogen;
      (iii) halide; and
      (iv) sulfur;
   (f) compounds of groups (a), (b), (c), (d), and (e) wherein one or more carbons are replaced by silicon.

7. The dosage form of claim 6 wherein each polyol monomer is independently selected from the group consisting of: 1,6-hexanediol, 1,7-heptanediol, tetraethylene glycol, triethylene glycol, and 1,2,6-hexanetriol.

8. The dosage form of claim 7 wherein the beneficial agent is ivermectin.

9. The dosage form of claim 8 wherein the poly(ortho ester) or polyacetal polymer is composed of the monomer residues of:
   (a) a diketene acetal or a divinyl ether; and
   (b) ivermectin; and
   (c) one or more other polyols.

10. The dosage form of claim 9 further comprising a poly(ortho ester) bond stabilizer or a polyacetal bond stabilizer selected from the group consisting of: carbonates, bicarbonates, organic amines, magnesium oxide, calcium oxide, magnesium hydroxide, and calcium hydroxide.

11. The dosage form of claim 10 wherein the polymer is a poly(ortho ester) composed of the monomer residues of:
   (a) 3,9-bis-(ethylidene)-2,4,8,10-tetraoxaspiro[5,5]undecane;
   (b) ivermectin;
   (c) tetraethylene glycol;
   (d) 1,6-hexanediol;
   (e) 1,2,6-hexanetriol.

12. The dosage form of claim 11 wherein the poly(ortho ester) bond stabilizer is magnesium oxide.

13. A bioerodible controlled release dosage form according to claim 1 wherein the ketene acetal or vinyl ether is diketene acetal or divinyl ether.

14. A bioerodible controlled release dosage form of claim 13 wherein the polymer is formed from the condensation of:
   (a) a diketene acetal or a divinyl ether; and
   (b) a beneficial agent having a hydroxyl functionality of two or more; and
   (c) one or more other polyols; and
wherein the beneficial agent is capable of being released from the polymer into the environment of use.

15. A method of treating a disease condition in a human or nonhuman animal, for those in need thereof, which comprises the implantation of a bioerodible controlled release device comprising a bioerodible polymer selected from a poly(orthoester) or a polyacetal in which a beneficial agent is covalently incorporated into a chain backbone of the polymer, wherein the beneficial agent
   (a) is capable of being released from the polymer into the environment of use; and
   (b) has a hydroxyl functionality of at least two; and the total equivalents of hydroxyl are present in stoichiometric ratios of 1 equivalent of hydroxyl to 0.1 to 1.5 equivalents of ketene acetal or vinyl ether.

16. A method of claim 15 wherein the disease is canine heartworm disease and the beneficial agent is ivermectin.

17. A dosage form according to claim 13 wherein the viscosity is maintained between 5000 and 50000 cp at 20° C. and 10 $sec^{-1}$, during the condensation reaction.

18. The method of claim 15 wherein the treatment is provided prophylactically to a human or nonhuman animal.

* * * * *